(12) United States Patent
Tanagho et al.

(10) Patent No.: US 7,306,627 B2
(45) Date of Patent: *Dec. 11, 2007

(54) ACELLULAR MATRIX GRAFTS OF COLLAGEN AND ELASTIC FIBER

(75) Inventors: Emil A. Tanagho, San Rafael, CA (US); Rajvir Dahiya, San Carlos, CA (US); Tom F. Lue, Hillsborough, CA (US); Gerald R. Cunha, Foster City, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/052,889

(22) Filed: Jan. 18, 2002

(65) Prior Publication Data

US 2002/0128711 A1 Sep. 12, 2002

Related U.S. Application Data

(62) Division of application No. 08/994,838, filed on Dec. 19, 1997, now Pat. No. 6,371,992.

(51) Int. Cl.
*A61F 2/08* (2006.01)

(52) U.S. Cl. ............... 623/14.13; 623/23.72; 600/36

(58) Field of Classification Search ........... 424/423, 424/558; 600/36; 623/23.76, 23.72, 23.74, 623/14.13
See application file for complete search history.

(56) References Cited

U.S. PATENT DOCUMENTS

| | | | | |
|---|---|---|---|---|
| 5,223,420 A | * | 6/1993 | Rabaud et al. ............ 424/425 |
| 5,523,291 A | * | 6/1996 | Janzen et al. ............ 514/21 |
| 5,554,389 A | * | 9/1996 | Badylak et al. .......... 424/558 |
| 5,595,571 A | * | 1/1997 | Jaffe et al. ............... 8/94.11 |
| 5,632,778 A | * | 5/1997 | Goldstein ................ 424/423 |
| 5,656,478 A | * | 8/1997 | Tanagho et al. .......... 435/378 |
| 5,676,698 A | * | 10/1997 | Janzen et al. ............. 623/8 |
| 5,756,350 A | * | 5/1998 | Lee et al. ................ 435/325 |
| 5,855,620 A | * | 1/1999 | Bishopric et al. ........ 128/898 |
| 5,916,265 A | * | 6/1999 | Hu ........................ 424/423 |
| 5,990,379 A | * | 11/1999 | Gregory ................. 128/898 |
| 5,993,844 A | * | 11/1999 | Abraham et al. ........ 424/423 |
| 6,371,992 B1 | * | 4/2002 | Tanagho et al. ........ 623/23.72 |
| 2005/0089544 A1 | * | 4/2005 | Khouri et al. ........... 424/426 |

OTHER PUBLICATIONS

Probst et al, "Reproduction of functional smooth muscle tissue and partial bladder replacement" British J. of Urology, 79 (4):505-515, (Apr. 1997).*

(Continued)

*Primary Examiner*—Paul B. Prebilic
(74) *Attorney, Agent, or Firm*—Townsend and Townsend and Crew LLP

(57) ABSTRACT

Acellular matrix grafts are provided with are isolated from natural sources and consist essentially of a collagen and elastin matrix which is devoid of cellular components. The grafts are useful scaffolds which promote the regeneration of muscle tissue and aid in restoring muscle function. Due to their acellular nature, the grafts lack antigenicity. As a result, the acellular matrix grafts can be isolated from autographic, allographic or xenographic tissues.

5 Claims, 3 Drawing Sheets

OTHER PUBLICATIONS

Probst, M., et al., "Reproduction of functional smooth muscle tissue and partial bladder replacement," British J. of Urology, 79(4):505-515 (Apr. 1997).

Furuto, D.K., et al., "Isolation and Characterization of Collagens and Procollagens," Methods in Enzymology, 144:41-61 (1987).

Rosenbloom, J., "Elastin: An Overview," Methods in Enzymology, 144:172-196 (1987).

Soskel, N.T., "Isolation and Characterization of Insoluble and Soluble Elastins," Methods in Enzymology, 144:196-214 (1987).

* cited by examiner

ACELLULAR MATRIX GRAFTS OF COLLAGEN AND ELASTIC FIBER

This application is a division of U.S. patent application Ser. No. 08/994,838, file Dec. 19, 1997, now U.S. Pat. No. 6,371,992.

This invention was made with Government support under Grant No. DK51101, awarded by the National Institutes of Health. The Government has certain rights in this invention.

BACKGROUND OF THE INVENTION

Bladder reconstruction plays an essential role in the treatment of voiding disorders characterized by low bladder capacity or high intravesical pressures or both-1 The ideal material should be biocompatible and mechanically reliable, resist extraluminal infection, deter or tolerate intraluminal infection, and be easy to implant surgically. The material should preserve renal function, provide adequate urinary storage at low pressure and allow volitional, complete evacuation of urine per urethram. To achieve this goal, autoaugmentation techniques and a great variety of synthetic and naturally derived biomaterials have been used.

Synthetic materials have been unsuccessful because of foreign-body reactions, resulting in stone formation, collapse, infection, rejection, or extrusion and migration of the graft (see Barrett, et al. *Semin. Urol.* 2:167-75 (1984); Bohne, et al. *J. Urol.* 77:725-732 (1957); Stanley, et al. *J. Urol.* 107:783-787 (1972); Swinney, et al. *Br. J. Urol.* 33:414-429 (1961)). As a result, synthetic materials have been used primarily as temporary implants to allow bladder regeneration to occur (see Taguchi, et al. *J. Urol.* 108:752-756 (1977); Tsuji, et al. *J. Urol.* 97:1021-1028 (1967)). However, the majority of studies confirm regeneration of transitional cell epithelial lining on the inner surface of the graft without adequate reconstruction of a functional detrusor muscle. Natural materials for bladder reconstruction have mostly retracted with time (see, Baret, et al. *Surg. Gynec. Obstet.* 97:633-639 (1953); Kelami, *J. Urol.* 105: 518-22 (1971)) and the alloplastic total bladder prosthesis is still at an investigational stage in animals.

Autoaugmentation by enterocystoplasty with either small bowel or colon has well-documented urodynamic benefits. Sidi, et al. *J. Urol.* 136:1201-4 (1986). Because of complications, including metabolic acidosis (McDougal, *J. Urol.* 147:1199-208 (1992)) rupture (Bauer, et al. *J. Urol.* 148: 699-703 (1992)), mucus production, chronic bacteriuria, stone formation (Golomb, et al. *Urology* 34:329-38 (1989)), and the potential for osteoporosis and malignancy (Filmer, et al. *J. Urol.* 143:671 (1990)), the search for other suitable materials continues. Gastrocystoplasty circumvents some of these problems, but peptic ulcers and perforations, the hematuria/dysuria syndrome, and metabolic alkalosis negate some of its potential advantages over intestinal segments. Mitchell, et al. Oxford, *Blackwell Scientific*, pp 439-444 (1993). Recently the technique for enterocystoplasty lined with urothelium has been shown to increase bladder capacity while taking advantage of the inert properties of an intact urothelial lining. Buson, et al. *Urology* 44:743-748 (1994); Gonzales, et al. *Urology* 45:124-129 (1995). Gastrointestinal segments in general have proven to enhance bladder capacity and compliance, thus protecting the upper tract and renal function. Unfortunately, they are unable to support normal micturition, which often necessitates clean intermittent catheterization or other supportive measures to ensure complete bladder evacuation.

To overcome this functional shortcoming, natural and/or biodegradable materials serving as a scaffold for the ingrowth of host bladder wall components have been tried with encouraging results. Atala, et al. *J. Urol.* 150:608-12 (1993); Knapp, et al. *J. Endourol.* 8:125-30 (1994); Novick, et al. *J. Biomed. Mater. Res.* 12:125-47 (1978); Scott, et al. *Br. J. Urol.* 62:26-31 (1988). The bladder wall tissue thus regenerated has shown the potential to provide functional augmentation in terms of an enlargement of the bladder without compromising its voiding abilities.

Despite the above efforts, there remains a need for new materials which are useful for grafting by serving as a scaffold for the development of new muscle tissue. The scaffolding material should be antigenic and capable of use in a variety of organs and individual hosts. Surprisingly, the present invention provides such materials and further provides methods for their preparation and use.

SUMMARY OF THE INVENTION

In one aspect, the present invention provides an acellular matrix graft which is isolated from muscle tissue, and consists essentially of acellular collagen and elastin. The muscle tissue which is the source of the graft is, for example, bladder tissue or other smooth muscle tissue such as heart tissue or ureter or urethra tissue.

In another aspect, the present invention provides methods of preparing acellular matrix grafts in which muscle or nerve tissue is isolated and freed from cells and cellular components by mechanical, chemical or enzymatic methods, or by combinations of mechanical, chemical and enzymatic methods to leave a scaffold or graft which is essentially collagen and elastin fibers. For example, a bladder acellular matrix graft can be prepared by:

(a) removing mucosa from an excised bladder cap to provide a bladder wall;

(b) treating the bladder wall with chemical and enzyme agents to release intracellular components from the bladder wall to provide an intermediate matrix; and (c) solubilizing and removing cell membranes and intracellular lipids from the intermediate matrix to provide a bladder acellular matrix graft which consists essentially of acellular collagen and elastin.

In yet another aspect, the present invention provides methods of restoring muscle function in animals having damaged or diseased muscles. In these methods, the damaged or diseased tissue is removed and replaced with an organ-specific acellular matrix graft. The surrounding tissue then grows and infiltrates the scaffold or graft such that muscle tissue is regenerated and muscle function is restored.

In one preferred embodiment, the method is directed to restoring bladder function in an animal having a partially damaged bladder, the method comprising:

(a) removing the portion of the bladder which is damaged; and (b) replacing the removed portion with a bladder acellular matrix graft to promote regeneration of bladder tissue and restore the bladder function.

In still another aspect, the present invention provides methods for promoting regrowth and healing of damaged or diseased muscle tissues, said method comprising replacing the damaged or diseased muscle tissue with an acellular matrix graft which consists essentially of acellular collagen and elastin, and is prepared from organ-specific tissue.

DETAILED DESCRIPTION

Figure 1:
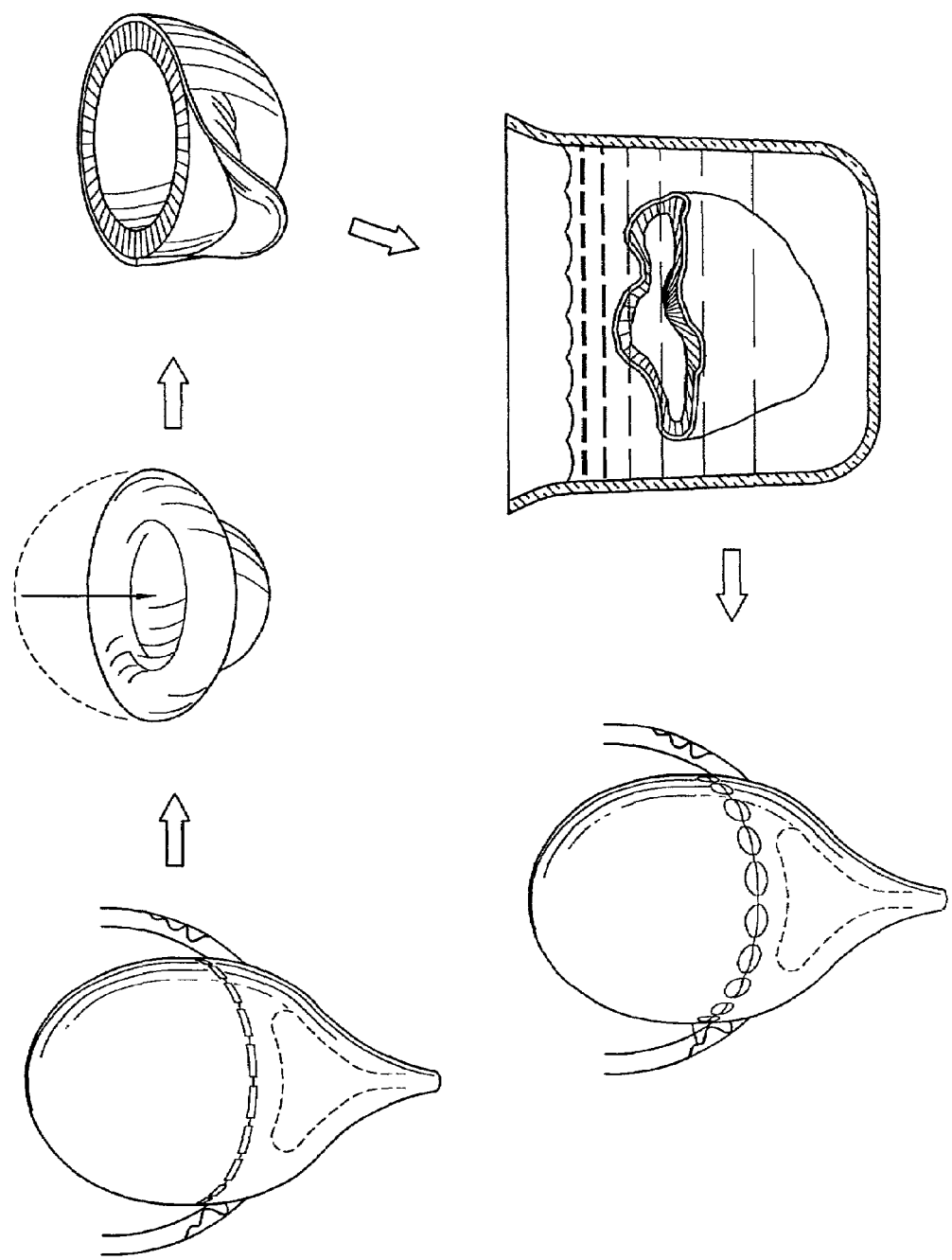
FIG. 1 illustrates the working steps for processing a native rat bladder into a bladder acellular matrix graft (BAMG).

The following abbreviations are used herein: DMEM, Dulbecco's modified Eagle's medium; RPMI, Roswell Park Memorial Institute media; HBSS, Hank's Balanced Salt Solution; FCS, fetal calf serum; EGF, epidermal growth factor; TGF-β, β-transforming growth factor; H&E, hematoxylin and eosin; PGP, peptide growth protein; DMSO, dimethylsulfoxide;

As used herein the term "allographic tissue" refers to tissue which is isolated from an individual and used in another individual of the same species. The term "xenographic tissue" refers to tissue which is isolated from an individual of one species and placed in an individual of another species. The term "autographic tissue" refers to tissue isolated from an individual which is grafted back into that individual.

The term "enzymatic digestion" refers to the degradation of tissues using enzymes such as nucleases. Typically, enzymatic digestion will be used to lyse cells and cellular components and remove the lysed products from the surrounding scaffolding of collagen and elastin.

The term "host" refers to an animal which is the recipient of tissue which has been purified, cultured and transplanted from another species (the donor) or from itself.

The term "acellular" in the context of a matrix refers to a composition that is essentially free of intact cells such that any remaining cells are not statistically or biologically meaningful in the ability of the matrix to perform as a regenerative support and is free of any unwanted cells that could include antigens which might contribute to rejection of the matrix by the immune system of the animal in which the matrix is introduced.

The term "xenograph or xenographic" refers to between species such as between rat and dog or pig and human.

The phrase "consisting essentially of" in the context of matrix compositions refers to a composition that includes elastin and collagen but does not include chemicals or naturally occurring compositions or cells which are derived from the source of origin of the matrix and that statistically or significantly contribute or improve the ability of the composition to perform as a substrate for regenerating cells; but, the phrase does include exogenously added incredients that substantially or significantly alter the grafting process as it relates to cell growth rates apart from the performance of the matrix. For example, the addition of growth factors to the matrix would still be included in the meaning of the phrase because the added ingredients act upon the invading cells directly and apart from the matrix and such factors do not act upon the matrix itself. Similarly, antibiotics would not alter the matrix performance but may indirectly improve its success rate by inhibiting growth of contaminating bacteria.

General:

Ideal materials for muscle replacement (e.g., partial bladder replacement) 20 should possess good physicochemical properties and mechanical reliability as well as biocompatibility. Bowel is most commonly used in various procedures of urinary diversion and neobladder replacement for the treatment of bladder cancer, neurogenic bladder dysfunction, bladder exstrophy, and interstitial cystitis. However, its use is not without long-term complications. See, for example, Bunyaratavey, et al. *J. Med. Assoc. Thai.*, 76:327 (1993) and Khoury, et al. *Urology*, 40:9 (1992). For this reason, the search for different materials and techniques for functional bladder replacement has long been the subject of a number of investigations.

Naturally derived materials for bladder wall substitution, such as lyophilized dura, have often been limited by their retraction over time (Kelami, *J. Urol.*, 105:518 (1971)) and the alloplastic replacement of the urinary bladder is still at an investigational stage in animals (Rohrmann, et al. *J. Urol.*, 156:2094 (1996)). Previous research has demonstrated that collagen-based materials, such as porcine small intestinal submucosa (SIS) (Knapp, et al. *J. Endourol.*, 8:125 (1994)) and polymer scaffolds with urothelial and smooth muscle cells (Yoo, et al. *J. Urol.*, 155:338 (1996)), have the best potential in terms of their regenerative capability and functional capacity. A new biomaterial, the bladder acellular matrix graft (BAMG) described in detail below and in Probst, et al. *Brit. J. Urol.*, 79:505 (1997), has recently been reported to be successful in rats for partial bladder replacement. The BAMG has now been demonstrated to provide complete regeneration of all wall components, and in vitro studies of matrix-regenerated muscle strips show approximately 50% contractility when compared with host strips (see, Piechota, et al. *Urol. Res.*, 25:2.12A (1997)). Because a BAMG can derive from mechanically, chemically and enzymatically processed native bladders of any species, a BAMG can be used as a homologous or xenogenic graft. Additionally, the acellularity of this graft material results in decreased antigenicity. Further provided herein is a demonstration that BAMG-regenerated rat detrusor smooth muscle actively contributes to in vivo storage and voiding while preserving the low-pressure reservoir function of the bladder. Still further, the contractility of the BAMG-regenerated bladders has been demonstrated with in vitro electrical and pharmacologic stimulation techniques.

Description of the Embodiments

In one aspect, the present invention provides a matrix graft consisting essentially of collagen and elastin. Preferably, the graft is an acellular matrix graft which is isolated from muscle tissue and which consists essentially of acellular collagen and elastin. The graft components (collagen and elastin) form a scaffold for the ingrowth of host components such as smooth muscle, blood vessels, and nerves. The acellular matrix graft can be isolated from a variety of sources such as bladder tissue, heart tissue, or ureter or urethra tissue and typically indicates essentially no cell nuclei when stained with dyes such as, for example, trichrome, H&E, α-actin and PGP. Preferred sources will depend on the anticipated use of the graft. For example, a preferred graft for bladder augmentation will be bladder tissue, which can be autographic, allographic or xenographic tissue. The most preferred sources of the matrix graft are those hosts which yield grafts of similar construction to the target recipient (considering, for example, the ratio of collagen to elastin fibers and the types of collagen fibers). Particularly suitable sources include tissues from rats, hampsters, dogs, pigs, rabbits, bovine and humans.

In a particularly preferred embodiment, the acellular matrix graft is a bladder acellular matrix graft (BAMG) which is isolated from rat, rabbit, hampster, dog, pig or human bladder tissue. As above, the graft is an acellular matrix consisting essentially of acellular collagen and elastin, and indicates essentially no cell nuclei when stained with trichrome, H&E, α-actin, or PGP dyes. In one preferred embodiment, the matrix graft is isolated from human bladder tissue and has an elastic modulus of about 0.40 to about 0.80 MPa. In another preferred embodiment, the matrix graft is isolated from rat bladder tissue and has an elastic modulus of about 0.80 to about 2.10 MPa. In yet another preferred embodiment, the matrix graft is isolated from pig bladder tissue and has an elastic modulus of about 0.25 to about 0.60 MPa.

The acellular matrix grafts can be prepared using known techniques for surgical removal of the source tissue and subsequent treatment of the tissue to remove cells and cell contents including cell membranes and intracellular lipids. FIG. 1 provides a schematic representation of the steps used in processing a rat bladder dome into a rat BAMG. In brief, the bladder dome is first surgically removed and inverted. Mucosa is removed by, for example, peeling or scraping, and the remaining lamina propria and muscularis is soaked in successive solutions of buffered preservatives, antibiotics, nucleases and detergents, e.g., sodium azide, DNAse, sodium deoxycholate and neomycin sulfate. The solutions serve to remove cellular material and preserve the BAMG until grafting. While the methods below are described with reference to bladder tissue, one of skill in the art will understand that similar steps can be applied to the isolation and preparation of acellular matrix grafts from other tissues and sources.

Accordingly, in another aspect, the present invention provides a method for the preparation of a bladder acellular matrix graft, comprising:

(a) removing mucosa from an excised bladder cap to provide a bladder wall;
(b) treating the bladder wall with chemical and enzyme agents to release intracellular components from the bladder wall to provide an intermediate matrix; and
(c) solubilizing and removing cell membranes and intracellular lipids from the intermediate matrix to provide a bladder acellular matrix graft.

In this aspect of the invention, mucosa is removed from an excised bladder cap. The bladder cap can be isolated from the sources indicated above, and preserved for later use, or it can be isolated just prior to processing. Removal of mucosa from the excised bladder cap will typically be carried out by first treating the tissue with sodium azide in PBS, then using manual techniques including, for example, gentle scraping with a suitable instrument or a glass slide. Other methods can also be used to remove the mucosa, including submucosa using similar methods but without peeling off the mucosa.

The resultant muscular wall which remains following removal of the mucosa is then treated with a combination of chemical and enzyme agents to initiate cell lysis thereby releasing cellular components and initiating the removal of cells from the matrix. A number of chemical and enzyme agents are known to be useful for effecting cell lysis. Suitable chemical agents include sodium azide, sodium chloride, sodium phosphate and potassium chloride. Typically, chemical treatment is carried out in a buffered aqueous solution (e.g., HEPES-buffered saline (HBS) or 1 M NaCl, 10 mM phosphate buffer) for a period of time of from about 1 to about 24 hours, more preferably about 3 to about 10 hours and most preferably about 5 to about 6 hours.

Enzyme agents which are useful in this aspect of the invention include nucleases such as, for example, DNase. Following cell lysis with the chemical and enzyme agents, an intermediate matrix is obtained.

The intermediate matrix is then treated to solubilize and remove any remaining cell membranes and intracellular lipids, thereby producing an acellular matrix graft. The treatments used to solubilize the cell membranes and intracellular lipids are typically chemical methods. In preferred embodiments, the chemical methods use a sodium desoxycholate solution containing sodium azide. More preferably, the solubilizing methods use an aqueous solution of from about 1% to about 8% desoxycholate, containing of from about 0.05% to about 5% sodium azide. In a particularly preferred embodiment, the cell membranes and intracellular lipids are removed from the intermediate matrix using an aqueous solution of about 4% sodium desoxycholate containing about 0.1% sodium azide. The period of time necessary to solubilize the cell membranes and intracellular lipids will depend on the temperature at which solubilization is carried out and the identity and concentration of the solubilizing agents. Typically, the solubilization is carried out at room temperature for a period of from about 1 to about 24 hours, more preferably about 3 to about 10 hours and most preferably about 5 to about 6 hours.

The resultant acellular matrix graft is typically washed with a physiologically compatible buffer (e.g., PBS) and used immediately, or it can be treated with a preservative (e.g., 0.1% sodium azide and 10% neomycin sulfate) and stored at about 4° C. until ready for use. One of skill in the art will appreciate that the processing steps described above for bladder tissue can be applied equally to the isolated and processing of other smooth muscle tissues such as urethra or ureter.

In yet another aspect, the present invention provides a method for promoting regrowth and healing of damaged or diseased muscle tissues. In this method, damaged or diseased muscle tissue is replaced with an acellular matrix graft prepared as described above. Accordingly, the diseased or damaged muscle tissue can be initially removed using surgical procedures, and an acellular matrix graft can be incorporated in its place. The removal of damaged or diseased muscle tissues can be accomplished using well-known surgical techniques such as, for example, partial cystectomy, augmentation cystoplasty, urethral stricture or ureter stricture. The replacement graft will typically be held in place using, for example, absorbable sutures, nonabsorbable sutures, or combinations of the two. Preferably, the sutures used are absorbable sutures.

An appropriate acellular matrix graft is typically one which has similar constituents and mechanical properties as the host tissue. The matrix graft can be xenographic, allographic or autographic. In order to more closely match the host tissues, allographic or autographic matrix grafts are preferred. When xenographic tissues are used for the preparation of an acellular matrix graft, the preferred origin of the acellular graft will be one which provides the nearest approximation to the recipient of collagen and elastin. The nearest approximation, or match, can be determined by subjecting the graft tissue to a variety of mechanical property tests.

To determine certain mechanical properties, matrix strips and a control are subjected to physical stress, using a system designed to apply a precise and reproducible load. Stress/strain curves can be generated (see Examples) and analyzed to describe the physical properties of the materials. For the bladder acellular matrix graft, the passive properties of strain, stress and elastic modulus are similar in the BAMG and the control bladder strips in all species (pig, human and rat were tested). Different strain values in the rat are due to the high amount of collagen type I and the lower amount of elastic fibers than in the pig and human. The tendency of the elastic modulus to be higher in the BAMG strips and the less balanced incline of the corresponding stress/strain graphs is a result of smooth muscle and urothelium loss. It has been noted in previous studies that age-related changes in collagen composition as well as structure (non-enzymatic glycosylation and increased crosslinking) may cause stiffening of the bladder wall (see Cerami, et al. *Sci. Am.*, 256:90 (1987); Monnier, et al. *Proc. Natl. Acad. Sci. USA*, 81:583 (1984); and Longhurst, et al. *J. Urol.*, 148:1615 (1992)).

Regeneration of the muscle tissue supported by the matrix graft typically includes angiogenesis, smooth muscle growth, and nerve proliferation. Angiogenesis, broadly defined as the growth of new capillary blood vessels from extant vascular beds, has been proposed to be regulated by a proliferative and/or morphogenetic pathway (type I collagen as a template for endothelial cell migration and lumen formation). Sage, H. E. et al. *J. Hypertens.*, 12:S145 (1994). Smooth muscle growth may originate from the edges of the graft or from pericytes after capillary neovascularization. Tilton, *J. Electron. Microsc. Tech.*, 19:327 (1991). Baskin, et al. (Baskin, et al., *J. Urol.*, 156:1820 (1996)) reported that both intact bladder urothelium and isolated bladder mesenchyme recombined with bladder urothelium from rat fetuses demonstrated expression of smooth muscle differentiation when grafted under the renal capsule. In contrast, bladder mesenchyme alone failed to induce smooth muscle expression when grafted. Additionally, the development of a functional extracellular matrix seems to be influenced by mechanical forces. The importance of an intact collagen scaffold has been underscored by the finding that physical strain stimulates collagen types I and III expression in bladder urothelial and smooth muscle cells. Baskin, et al., *J. Urol.*, 150:601 (1993)). Although collagen type I promotes cell migration, differentiation and tissue morphogenesis during development (Brenner, et al., *J. Lab. Clin. Med.*, 124:755 (1994)), its main function in connective tissues has been assumed to be withstanding tension (see, Montes, *Cell Biol. Int.*, 20:15 (1996)). Collagen type III is thought to be responsible for structural maintenance in expansible organs. The histology of the matrix grafts presented demonstrates different features in texture. However, although different quantities of collagen types I and III have been shown, both types have been found as major components of the BAMG.

Because active function of the bladder seems mainly to be generated by smooth muscle cells, the tensile properties have been assumed to be influenced by the extracellular matrix. Pasquali-Ronchetti, I. et al.: Ultrastructure of elastin. In: Ciba Foundation Symposium on the molecular biology and pathology of elastic tissues, New York: John Wiley & Sons, pp 31-42, 1995. Elastic fibers are most abundant in tissues subject to stretching, such as blood vessels, lung, skin and elastic cartilage (Viidik, A. et al. *Biorheology*, 19:437, 1982), while the collagen network seems to be responsible for the quality of high tensile strength in connective tissues. Jain, M. K. et al. *Biomaterials*, 11:465, 1990.

Xenotransplantation of the matrix graft can show variations in the degree and quality of smooth muscle regeneration (see, Piechota, H. J. et al. *Urol. Res.*, 25:2.12A, 1997). When hamster and pig BAMGs are grafted to rat bladder, regeneration is best facilitated with the closest possible structural match between the matrix graft and the host bladder wall. This has been confirmed by the differences in the pure matrix structures presented herein. The similar performance of the pig BAMG with the human BAMG allows the use of pig BAMG material for partial bladder replacement in humans.

Accordingly, in still another aspect, the present invention provides a method of restoring bladder function in an animal having a partially damaged bladder, the method comprising:
(a) removing the portion of the bladder which is damaged; and
(b) replacing the damaged portion with a bladder acellular matrix graft to promote regeneration of bladder tissue and restore the bladder function.

In this method, the animal which is being treated can be a rat, pig, dog, or human. Typically, the bladder acellular matrix graft is prepared, as described above, from xenographic or allographic tissue.

The present invention further provides methods of restoring muscle function in an animal having a partially damaged muscle, the method comprising:
(a) removing the portion of the muscle which is damaged; and
(b) replacing the damaged portion with an acellular matrix graft to promote regeneration of muscle tissue and restore the muscle function.

In this method, as in the methods above, the animal which is being treated can be a rat, pig, dog, or human. Typically, the acellular matrix graft is prepared, as described above, from xenographic or allographic tissue. Preferably, the acellular matrix graft is prepared, as described above, from organ-specific xenographic or allographic tissue. For example, repairing heart muscle in a human will preferably be accomplished with an acellular matrix graft from heart tissue of a donor which is preferably human or another mammalian species which provides a matrix graft similar in composition to a human heart acellular matrix graft.

The following experimental results are offered by way of example and are not meant to limit the scope of the invention.

EXAMPLES

Example 1

This example illustrates the preparation and characterization of bladder acellular matrix grafts from rat, pig and human bladders.

1.1 Bladder Isolation

Urinary bladders without the trigone were harvested from fresh rat (female, age 5 months, N=20) and pig (female, age 9 months, N=3) and a female human cadaver (age 65 years). The pig and human bladders were longitudinally bisected; half was assigned for matrix preparation, and the other for control. The rat bladders were not bisected; 10 were assigned to each group.

1.2 Acellular Bladder Matrix Preparation

In the matrix preparation process, urinary bladders were placed in Petri dishes containing 50 mL of 10 mM phosphate-buffered saline (PBS, pH 7.0) and 0.1% sodium azide. The bladders were inverted and the mucosa was scraped off with a pair of glass slides. The remaining lamina propria and detrusor muscle were treated with 50 mL of 10 mM PBS—0.1% sodium azide and stirred for 5-6 hours to obtain partial cell lysis. Bladders were then washed with 40 mL of PBS before treatment with 50 mL of 1 M sodium chloride containing 2000 Kunitz units DNase (Sigma; St. Louis, Mo.) and then stirred for 12-14 hours; this step was repeated 2 to 4 times depending on the source of bladder. With this, cell lysis was complete and all the intracellular components were released. The samples were then treated with 50 mL of 4% sodium deoxycholate containing 0.1% sodium azide and stirred for 5-6 hours to solubilize the lipid bilayer cell membranes and intracellular membrane lipids; this step was repeated twice. The resultant bladder acellular matrix graft was washed three times with 50 mL PBS and stored in 0.1% sodium azide and 10% neomycin sulfate at 4° C.

1.3 Light Microscopy

Acellular graft specimens were fixed in 10% buffered formalin for at least 24 hours. After dehydration in graded ethanol, the specimens were embedded in paraffin (sections: 5 µm) and stained with hematoxylin and eosin (H&E) for nuclei and α-actin for smooth muscle. These studies showed the structures of the matrices (rat, pig and human) to be an acellular scaffold and thus confirmed the effectiveness of the matrix preparation process. The elastic fibers were stained according to Hart's technique. see, Luna, Manual of Histologic Staining Methods of the Armed Forces Institute of Pathology, 3rd ed. New York: McGraw Hill Book Co., pp 79-80 (1968). Collagen types were identified as reported by Junqueira et al., *Cell Tissue Res.*, 202:453 (1979). Histologic sections were stained with Sirius red and viewed under polarized light (thick fibers [type I] appear strongly birefringent yellow or red, and thin fibers [type III] appear greenish and are weakly birefringent). Elastic fibers were seen in the bladder matrix of all three types, and histologic differences were apparent in both elastin and collagen fibers. In the pig, and particularly the human matrix, the number of elastic fibers was greater than in the rat. Picrosirius-stained specimens under the polarizing microscope demonstrated that type I was the major collagen fiber in the rat bladder matrix. In contrast, type III fibers were abundant in the pig and human bladder matrix. The ratio of thick to thin collagen fibers in the rat BAMG was notably higher than in the pig or human BAMG.

1.4 Transmission Electron Microscopy

Specimens were immersed in a fixative (2.5% glutaraldehyde and 2.5% paraformaldehyde) in 0.15 M sodium cacodylate buffer. After primary fixation, the samples were placed in a drop of fixative on dental wax and cut in 3 mm segments. Specimens were post-fixed in 2% osmium tetroxide, block-stained in tannic acid, and dehydrated in a graded series of ethanol and propylene oxide, after which they were embedded in resin. Thin sections (500 Å) were cut and mounted on 200-mesh copper grids. After staining in uranyl acetate and lead citrate, examination with a Philips 400 Model electron microscope was carried out.

Electron microscopic studies disclosed variations in the structure of the acellular matrix scaffold in the different species and supported light microscopic findings. There were notably fewer elastic fibers in the rat bladder matrix than in the pig and human matrix, and they appeared to be more densely stained. Collagen fibers appeared to be closely packed with marked variations in diameter in the rat matrix; in the pig, and particularly the human, they appeared as a loose network. Electron microscopy was not able to distinguish distinct collagen types.

1.5 Strip Preparation and Mechanical Properties

Specimens were assigned to six groups (N=10 in each): viz., the normal bladder and the acellular matrix of each of the three species. Longitudinal strips were obtained from each group. A sandpaper frame was constructed around the specimens to facilitate uniform gripping during tensile testing. The ends of each strip were attached to the smooth side of the sandpaper with cyanoacrylate adhesive to prevent slippage from the clamps. Subsequently, another sandpaper frame was attached to form a sandwich around the strip with a window over the test section. Specimens were wrapped in saline-moistened gauze, covered in plastic wrap, and stored at −20° C.

Before testing, specimens were removed from the freezer and allowed to thaw while immersed in physiologic saline at room temperature. Both length and width of the specimens were measured with Verner calipers (±0.02 mm). The width of the specimen was also measured within the frame. The frames were mounted in the grips of a servohydraulic material testing machine (MTS Bionix 858, Eden Prairie, Minn., USA). Once mounted in the grips, the sides of the sandpaper frame were cut. The specimens were distracted longitudinally at a rate of 0.3 mm/sec to failure. Specimen load and grip travel were continuously measured throughout the tests with a precision force transducer (Sensotec, Model 31, Columbus, Ohio.) and the test system Linear Variable Differential Transformer (LVDT).

Stress/strain curves for each specimen were generated and the ultimate tensile strength, maximum strain and elastic modulus were determined. The strength (MPa) was calculated by dividing the failure load by the cross-sectional area of the specimen. The maximum strain, i.e. the strain value corresponding to the ultimate strength, was calculated as the displacement of the specimen divided by the initial gauge length (in mm/mm). The elastic modulus (MPa) of the strips was defined as the slope of the most linear region of the stress/strain curve. Photographs of each test were taken to analyze the failure patterns of each specimen. Data are given as mean±S.D. Differences between the means of the BAMG and control urinary bladder were tested for statistical significance with Student's t-test. A value of $p \leq 0.05$ was considered significant.

The mechanical properties of the rat, pig and human BAMG and control urinary bladder strips are summarized in Table 1.

TABLE 1

Tensile Properties of the BAMG versus the Normal Urinary Bladder in Rat, Pig and Human

| Material | No. | Ultimate Tensile Strength (mm/mm) | Ultimate Tensile Strength (MPa) | Elastic Modulus (MPa) |
|---|---|---|---|---|
| Rat BAMG | 10 | 0.73 ± 0.23* | 0.68 ± 0.21 | 1.43 ± 0.59* |
| Rat Bladder | 10 | 2.03 ± 0.44 | 0.72 ± 0.21 | 0.76 ± 0.44 |
| Pig BAMG | 10 | 1.86 ± 0.51 | 0.29 ± 0.05 | 0.40 ± 0.13 |
| Pig Bladder | 10 | 1.66 ± 0.31 | 0.32 ± 0.10 | 0.26 ± 0.18 |
| Human BAMG | 10 | 0.91 ± 0.08 | 0.13 ± 0.05 | 0.60 ± 0.21 |
| Human Bladder | 10 | 0.69 ± 0.17 | 0.27 ± 0.14 | 0.25 ± 0.18 |

Data are given as mean ± S.D.
*p < 0.05 vs. normal rat bladder

There was no evidence of specimen slippage within the grids during the testing procedure. The site of failure during testing varied and depended on the architecture of the particular specimen, near the ends in some cases and within the center of the strip in others.

Typical stress/strain plots for the BAMG and the control bladder strips demonstrated an initial nonlinear region, followed by a linear region, and finally a region where failure occurred in all species. The incline of the BAMG graphs was less balanced than that of the control bladder strips in all species.

The mean maximum strain for the BAMG and the control bladder strips was not significantly different, except in the rat ($p<0.05$). Also there was no significant difference in the ultimate strength between the BAMG and the control strips in all species ($p>0.05$); however, the ultimate tensile strength of both the rat bladder and the rat BAMG was higher than that of the pig and human groups.

The comparison of the elastic modulus for the BAMG and the control bladder strips did not show any significant difference in either the pig or human specimens ($p>0.05$), although, in general, the BAMG had a higher value than the control. In contrast, the elastic modulus of the rat BAMG was significantly higher than the value for the control rat bladder strips ($p<0.05$). The elastic moduli for both the rat bladder and the rat BAMG were higher than those for the pig and human groups.

The biomechanical properties of the newly developed bladder acellular matrix graft support its use for bladder replacement. Variations of the matrix structure in different species indicate that the closest possible structural match between the matrix graft and the host bladder wall will achieve the best functional results.

Example 2

This example illustrates the decreased antigenicity of the bladder acellular matrix graft (BAMG) through xenotransplantation and also evaluates the in vivo and in vitro functional properties of the BAMG-regenerated rat urinary bladder.

2.1 Preparation of the Bladder Acellular Matrix Graft (BAMG)

Bladders from male Syrian hamsters, male New Zealand white rabbits, and male mongrel dogs were obtained from our institutions' tissue-sharing program. The bladders were excised and treated essentially as described in Example 1. The hamster BAMGs were used as full-bladder-size grafts, whereas rabbit and dog BAMGs were cut to smaller patches of approximately 5×5 mm before grafting.

Figure 2:
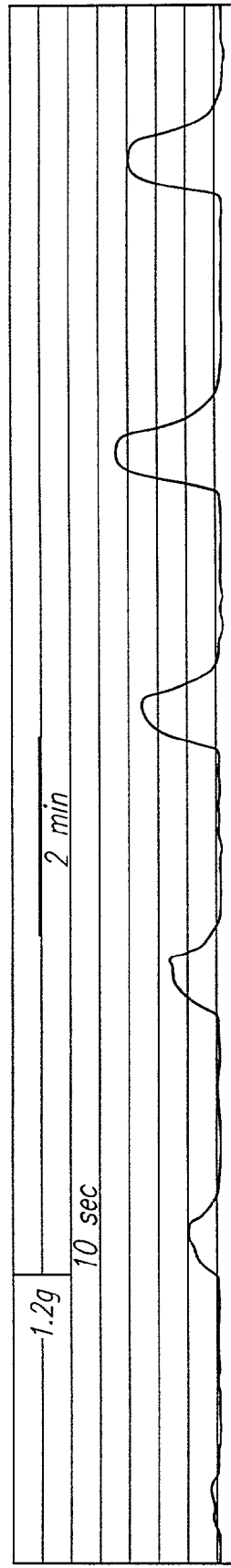
FIG. 2 shows the recordings of electrical field stimulation in a hamster BAMG regenerate and a corresponding host bladder smooth muscle strip 4 months after grafting.
Figure 2:
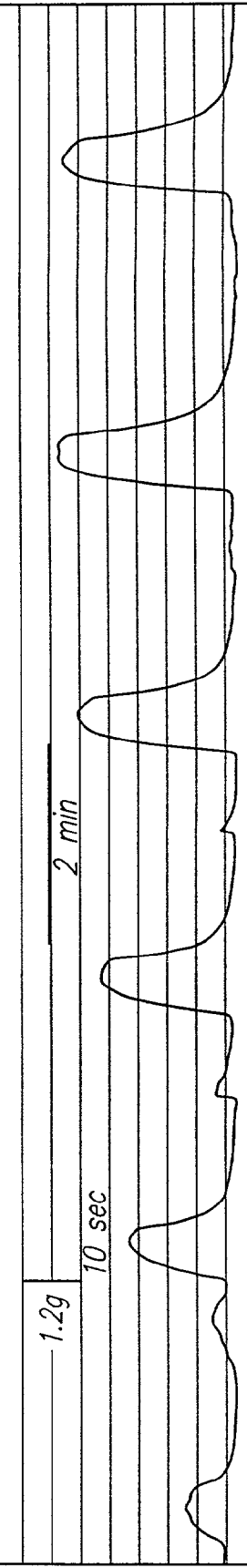

Histologic sections were examined by light and scanning electron microscopy before grafting to confirm the BAMGs' acellularity and thus the effectiveness of the matrix preparation process. These studies revealed an intact framework of collagen and elastin fibers with no evidence of remaining cells, nuclei or other cell fragments. The structure, density and thickness of the fibers differed considerably among the three BAMG types. The average fiber diameter seemed to increase with the size of the BAMG donor species; fiber density appeared to be less in the rabbit and dog BAMGs than in the hamster BAMG (FIG. 2).

2.2 Surgical Technique

Male and female Sprague Dawley rats (n=20) were anesthetized with pentobarbital (40 mg/kg i.p.) and placed supine on a warmed operating table (37° C.). Through a lower midline incision, the bladder was exposed and a 70% cystectomy was performed without coagulation or ligation of the vessels. The previously prepared BAMG was grafted to the remaining host bladder with a continuous polyfilament-coated 8-0 Vicryl™ (Ethicon Inc., Somerville N.J.) absorbable suture for both the anterior and posterior walls. Four nonabsorbable monofilament 7-0 Dermalon™ (Davis+Geck, Manati PR) button sutures were placed—one each at the anterior, posterior, left and right sides—to identify the matrix borders. The control animals (n=10) underwent partial cystectomy only. Three 7-0 Dermalon™ button sutures were placed at the left, mid and right sides for later identification of the site of cystectomy.

The hamster, rabbit and dog BAMGs were grafted to 20 Sprague-Dawley rats (the distribution of male to female was 3 to 2 within each group). Five animals died postoperatively (3 male, 2 female). The 3 male rats (2 hamster and 1 rabbit BAMG) died within 2-4 days from uremia consequent to urinary extravasation into the abdominal cavity. All 3 presented with complete obstruction of the bladder neck and proximal urethra by a staghorn stone-like plug formed of coagula and defurfurated fibers of the BAMG (non-mineral material, as shown by both polarizing light microscopy and scanning electron microscopy). Leakage always occurred at the site of anastomosis. A rupture of the graft itself was never seen. The 2 female animals (1 rabbit and 1 dog BAMG) died 3 weeks after surgery from a Corona virus infection associated with severe respiratory tract obstruction and rapid weight loss. A total of 15 grafted rats were available for further evaluation.

Partial cystectomy was performed in 10 control rats (5 male/5 female). None of the animals died of causes related to the surgical procedure itself. However, 3 rats died within 2 hours postoperatively of respiratory failure while suffering from a Corona virus infection. The 7 surviving rats (3 male/4 female) were available for follow-up.

In female rats, the grafted bladder was tested for leakage by instillation of saline through a urethral tube. Because atraumatic catheterization is extremely difficult in male rats, the bladder was filled with a 27-gauge hypodermic needle through the posterior host bladder wall. When satisfactory closure was achieved, the abdominal wall and the skin were closed in two layers, with 4-0 plain gut (Davis+Geck) and 3-0 braided silk (Ethicon), respectively. No drainage was used and no drugs were administered peri- and postoperatively.

All animals were sacrificed 4 months after surgery. Two bladders of each group were saved for histologic evaluation only. The bladders were filled with 10% formalin after ligation of both ureters and urethra, thus allowing fixation in a distended state. The remaining bladders were subjected to immediate tissue bath studies and histologic evaluation thereafter.

Only 29% of the control rats presented with the formation of 1 to 7 bladder stones, in contrast to almost 85% of the grafted animals. Stone formation was especially pronounced in the hamster BAMG-grafted animals (6 to 32 calculi). However, the composition of the calculi (struvite, 60-100%; apatite, 40-100%; Newberryite, 20-100%; and brushite, 10-100%) did not differ among the control and the grafted groups.

2.3 Evaluation of Micturition Pattern

Volumes per void were evaluated non-invasively in all animals preoperatively and at 3 and 7 days and 1, 2, 3 and 4 months after surgery. A specially designed "micturition cage" was used. The cage consisted of four standard "banging-basket" housing cages (10×8 inches) with a 0.5-inch metal grid bottom. These were placed on wooden supports (space maintainers) on a rack featuring a siliconized ⅛-inch hardware cloth, which effectively prevented stool particles from falling into the collecting trays while not hindering free passage of urine. The collecting trays were made of waste X-ray films chosen because the material is stiff, lightweight and water-repellent. The trays covered the entire area under each cage and were suspended by four nylon strings to isometric force displacement transducers (Omega Engineering Inc., Stamford Conn.) whose range of detection was 0.1 to 65 mg of urine. An SCXI-1121 signal processor (National Instruments Corp., Austin Tex.) supplied the excitation voltage to the transducers and fed the analog force data to an NB-MIO-16 analog-to-digital converter (National Instruments). A Macintosh Quadra 800 personal computer was used for data acquisition. With the Laboratory Virtual Instrument Engineering Workbench software program (LabView®, National Instruments), a 4-channel virtual instrument was designed to collect and display the digitalized data and to save it in a spreadsheet format transferable to the Microsoft Excel software program, thus facilitating graphic and statistical analysis.

Because approximately two-thirds of all voids in rats occur at night (Eika, et al. *J. Urol.* 151:496-502 (1994)), urinary excretion, voiding frequency and volumes per void were studied for 12 hours overnight. All rats were allowed to equilibrate in the housing cages for 8 to 10 hours with food and water given ad libitum. To enhance diuresis, no food but a sweetened orange-flavored instant drink (Tang™, Kraft General Foods Inc., White Plains N.Y.) was offered during the 12-hour study period.

Although mean preoperative volumes per void were slightly higher in the partial cystectomy group, this difference was not statistically significant (p=0.055 vs. the hamster BAMG group). Three days after grafting, volumes per void were decreased by more than 50% in all animals. Within 2 months they were gradually restored; at the end of the 4-month observation period, they exceeded preoperative values by 94% in the grafted animals and 35% in the control group. The difference from control in absolute volume per void was not statistically significant, however (dog BAMG, p=0.061; hamster BAMG, p=0.458; rabbit BAMG, p=0.159) (Table 2).

TABLE 2

Volumes per Void After Partial Cystectomy and in BAMG-regenerated Rat Bladders Within 4 Months of Surgery

|  | Hamster BAMG (n = 5) | Dog BAMG (n = 5) | Rabbit BAMG (n = 5) | Partial Cystectomy (n = 7) |
|---|---|---|---|---|
| Pre-operative | 0.47 ± 0.06 | 0.57 ± 0.07 | 0.51 ± 0.05 | 0.65 ± 0.04 |
| 3 Days postop. | 0.25 ± 0.01 (−53%)* | 0.37 ± 0.03 (−64%) | 0.28 ± 0.02 (−55%) | 0.34 ± 0.02 (−52%) |
| 1 Week postop. | 0.37 ± 0.07 | 0.48 ± 0.03 | 0.36 ± 0.01 | 0.47 ± 0.02 |
| 1 Month postop. | 0.41 ± 0.07 | 0.67 ± 0.05 | 0.66 ± 0.03 | 0.64 ± 0.04 |
| 2 Months postop. | 0.63 ± 0.09 | 0.72 ± 0.04 | 0.71 ± 0.12 | 0.80 ± 0.06 |
| 3 Months postop. | 0.76 ± 0.08 | 0.99 ± 0.12 | 1.04 ± 0.15 | 0.82 ± 0.05 |
| 4 Months postop. | 0.81 ± 0.11 (+72%) | 1.08 ± 0.10 (+90%) | 0.99 ± 0.06 (+94) | 0.88 ± 0.06 (+35%) |

All data are expressed as mean value ± S.E.M.
*Percentages of preoperative values are given in italics.

Fluid consumption and consequent urine excretion increased 2.2-fold in the grafted and 1.3-fold in the control animals during the 4-month observation period. Voiding frequency initially increased by 42% in the grafted and 77% in the control group. At 4 months after surgery, voiding frequency was almost the same as pre-operatively in all groups.

2.4 Cystometric Measurements

Cystometric evaluation was performed at 4 months according to a method modified from Malmgren et al. (Malmgren, et al. *J. Urol.* 137:1291-1294 (1987)) and Dorr (Dörr, *J. Urol.* 148:183-187 (1992)). All rats were anesthetized with urethane (1.100 mg/kg i.p.) and placed supine on a warmed operating table. In female rats, transurethral cystometry was performed by means of a 24-gauge angiocatheter connected by polyurethane tubing (PE-90) to a pressure transducer (Baxter Uniflow pressure transducer, Baxter Healthcare Corp., Irvine Calif.). An SCXI-1121 signal processor (National Instruments Corp., Austin Tex.) supplied the excitation voltage to the transducer and fed the analog pressure data to an SCXI-1000 analog-to-digital converter (National Instruments). A Macintosh Quadra 800 personal computer with the LabView® software program (National Instruments) was used to acquire data and save it in spreadsheet format. In male rats open cystometry was performed. The PE-90 tubing with a cuff at its tip was inserted through a small incision in the lower ventral bladder wall where it was fixed with a 7-0 Dermalon™ tobacco sac suture. Before the experiments were begun, the pressure transducers with tubing and angiocatheter attached were zeroed to the atmosphere during infusion. The bladder was emptied before each cystometric measurement. After an equilibration period of 15 minutes, each rat underwent five consecutive cystometric measurements during infusion of warmed saline (37° C.) at 0.2 mL per minute with a Harvard Apparatus 22 pump (Harvard Apparatus, Millis Mass.). Upon infusion, capacity was determined as the volume at which any kind of leakage occurred. Baseline pressures, bladder opening pressures and peak pressures were measured. Compliance (cm $H_2O$/mL) was calculated according to the formula:

$$\frac{P_2 - P_1}{V_2 - V_1}$$

with $P_2$ representing the bladder opening pressure and $V_2$ the infused volume at that time and $P_1$ representing the baseline pressure and $V_1$ the infused volume at that time. Hence, high values reflect poor compliance, while small values characterize good bladder compliance. 5 Slight differences in baseline pressure proved not to be statistically significant (Table 3).

TABLE 3

Cystometric Findings After Partial Cystectomy and in BAMG-regenerated Rat Bladders 4 Months Postoperatively

|  | Baseline Pressure (cmH$_2$O) | Bladder Opening Pressure (cmH$_2$O) | Peak Pressure (cmH$_2$O) | Capacity (ml) | Compliance (cmH2O/ml) |
|---|---|---|---|---|---|
| Hamster (n = 5) BAMG | 4.4 ± 0.4 | 21.2 ± 1.8 | 43.3 ± 3.0 | 2.49* + ± 0.04 | 11.5* + ± 1.6 |
| Dog (n = 5) BAMG | 4.1 ± 0.9 | 19.2 ± 1.2 | 34.3 ± 2.8 | 2.23* + ± 0.09 | 8.8* ± 0.8 |
| Rabbit (n = 5) BAMG | 2.3 ± 0.8 | 20.8 ± 0.8 | 41.8 ± 0.7 | 2.08* + ± 0.04 | 9.9* ± 1.6 |

TABLE 3-continued

Cystometric Findings After Partial Cystectomy and in BAMG-regenerated Rat Bladders 4 Months Postoperatively

|  | Baseline Pressure (cmH$_2$O) | Bladder Opening Pressure (cmH$_2$O) | Peak Pressure (cmH$_2$O) | Capacity (ml) | Compliance (cmH2O/ml) |
|---|---|---|---|---|---|
| Partial (n = 7) Cystectomy | 3.7 ± 2.2 | 19.3 ± 1.5 | 47.4 ± 2. | 1.43 ± 0.08 | 24.8 ± 1.0 |

All data are expressed as mean value ± S.E.M.
*: significant difference (p < 0.05) when compared with the partial cystectomy group.
+: significant difference (p < 0.05) when compared with other BAMG-regenerated bladders.

The bladder opening pressure was almost identical in all groups. The peak pressure was the highest in the partial cystectomy group, followed by the hamster and rabbit BAMG groups, with the lowest values in the dog BAMG-regenerated bladders; these differences were not statistically significant (p≧0.154). In contrast, bladder capacity was significantly higher than the control in all grafted animals (hamster BAMG, p=3.39×10$^{-7}$; dog BAMG, p=2.10×10$^{-5}$; rabbit BAMG, p=0.012). The differences in bladder capacity among the grafted groups were also statistically significant (hamster vs. dog BAMG, p=0.027; dog vs. rabbit BAMG, p=3.66×10$^{-7}$). Compliance was significantly decreased in the partial cystectomy group (p<1.96×10$^{-4}$). Among the grafted groups, the hamster BAMG-regenerated bladders were significantly less compliant than the dog BAMG-regenerated bladders (p=0.03). Bladder calculi might have interfered with the cystometric measurements to varying degrees. Furthermore, bladder hypertrophy consequent to excessive stone formation might have adversely affected compliance in the hamster BAMG-regenerated bladders.

2.5 Tissue Bath Experiments

Tissue Preparation: The excised bladders were placed in a Petri dish with chilled Krebs solution and carefully dissected free from the adherent connective tissue. Muscle strips of the same size (2×7 mm) of the regenerated bladder dome and the host bladder side wall were obtained. These were mounted in the tissue bath to a glass tissue support hook (Radnoti Glass Technology, Monrovia Calif.) on one side and an isometric force displacement transducer, (Radnoti Glass Technology) on the other by means of two spring-wire clips connected with 4-0 braided silk. All preparations were sufficiently durable to withstand the grip of the wire clips during repeated or continuous contractions.

Bladder stone formation is a common finding after lower urinary tract surgery in the rat. Guan, et al. *J. Urol.* 461-5; discussion 474 (1990); Kropp, *Urology* 46:396-400 (1995); Liang, et al. *Invest. Urol.* 12:5-7 (1974); Little, et al. *J. Urol.* 152:720-724 (1994); Vaught, et al. *J. Urol.* 155:374-8 (1996). Indeed, this was true for the majority (85%) of grafted animals in our study. Bladder calculi may eventually cause chronic inflammation and/or hypertrophy and dilation of the bladder through outlet obstruction, potentially affecting not only the in vivo voiding characteristics but also the in vitro contractility. To ensure the same starting point for our organ bath experiments, we compared the BAMG-regenerated smooth muscle strips to strips from the same host bladder wall rather than to bladder strips from untreated agematched control rats. Although all strips were cut about the same size, the regenerated and host bladder strip weights varied considerably. Differences in muscularization and collagen content and/or bladder hypertrophy are possible explanations for this phenomenon. The peak contraction values (Table 4) were therefore related to the weight of each individual muscle strip.

TABLE 4

Organ Bath Findings in BAMG-Regenerated Rat Bladder Strips 4 Months After Grafting

|  |  | Strip Weight (mg) | Resting Tension (gm) | Maximum Forces of Contraction Electrical Field Carbachol High Potassium (mNewton/mg of bladder wall tissue) | | |
|---|---|---|---|---|---|---|
| Hamster | Matrix (n = 4) | 47.6 + ± 4.2 | 0.78 ± 0.03 | 0.26* ± 0.07 | 0.59* ± 0.01 | 0.12 ± 0.02 |
|  | BAMG Host Strips (n = 10) | 37.8 ± 2.5 | 0.73 ± 0.08 | 0.62 ± 0.12 | 1.19 ± 0.22 | 0.41 ± 0.11 |
| Dog | Matrix (n = 4) | 34.3 ± 3.6 | 0.9 ± 0.01 | 0.34 ± 0.02 | 0.61 ± 0.02 | 0.31 ± 0.01 |
|  | BAMG Host Strips (n = 10) | 53.6 ± 5.6 | 0.82 ± 0.05 | 0.40 ± 0.09 | 1.091 ± 0.19 | 0.36 ± 0.10 |
| Rabbit | Matrix (n = 4) | 23.4 ± 1.1 | 0.78 ± 0.08 | 0.30* ± 0.05 | 0.61* ± 0.14 | 0.20 ± 0.03 |
|  | BAMG Host Strips (n = 10) | 34.0 ± 3.6 | 0.71 ± 0.07 | 0.80 ± 0.06 | 1.79 ± 0.16 | 0.45 ± 0.12 |

All data are expressed as mean value ± S.E.M.
*: significant difference (p < 0.05) when compared with host bladder smooth muscle strips.
+: significant difference (p < 0.05) when compared with other BAMG regenerate strips.

Tissue Bath and Recording and Stimulating Equipment: The 30-mL double-chambered Quiet Bath (Radnoti Glass Technology) was used. Its working chamber was connected to a second chamber with 95% oxygen and 5% $CO_2$ infusion. Gas flow induced circulation of the Krebs solution, which was warmed to 37° C. by an external heating circuit (circulating pump Thermomix BU, Braun Instruments, Burlingame Calif.). Forces lower than 1 mNewton (0.1 g) without bubble artifacts could be measured in the working chamber. The transducer signals were fed into a thermal array recorder (Gould TA 4000, Gould Inc., Valley View Ohio). For tissue stimulation, vertical L-shaped, custom-made platinum iridium electrodes (15 mm long, 0.18 mm diameter) separated by 10 mm were used with a Grass S44 stimulator (Grass Instrument Co., Quincy Mass.). The tissue was mounted parallel to the electrodes at a preload of 20 mNewton (2 g) resulting in a resting tension of about 4 mNewton (0.4 g) at the end of a 60-min equilibration period. A custom-made current-distribution box supplied a supramaximal current of 0.14 A at 15 V, which was sequentially delivered to two of eight chambers.

Electrical Field Stimulation: On the basis of preliminary length-tension, frequency-response and current-response studies of normal rat detrusor smooth muscle, we used the following supramaximal stimulation parameters: bipolar, monophasic balance-charged rectangular pulses; 1 msec pulse duration; 1-80 pulses per second (pps) frequency; 10 sec stimulation trains; 2 min intervals between stimulations; 0.14 A amplitude at 15 V.

Electrical field stimulation was used to evaluate nerve-mediated smooth muscle contraction. Carbachol (as the classic cholinergic agonist) and atropine (as the appropriate antagonist) were used to demonstrate functionally the presence of cholinergic receptors within the regenerated tissue.

Potassium was used as another mechanism to induce smooth muscle cell depolarization through a direct chemical change of the membrane potential.

Figure 3:
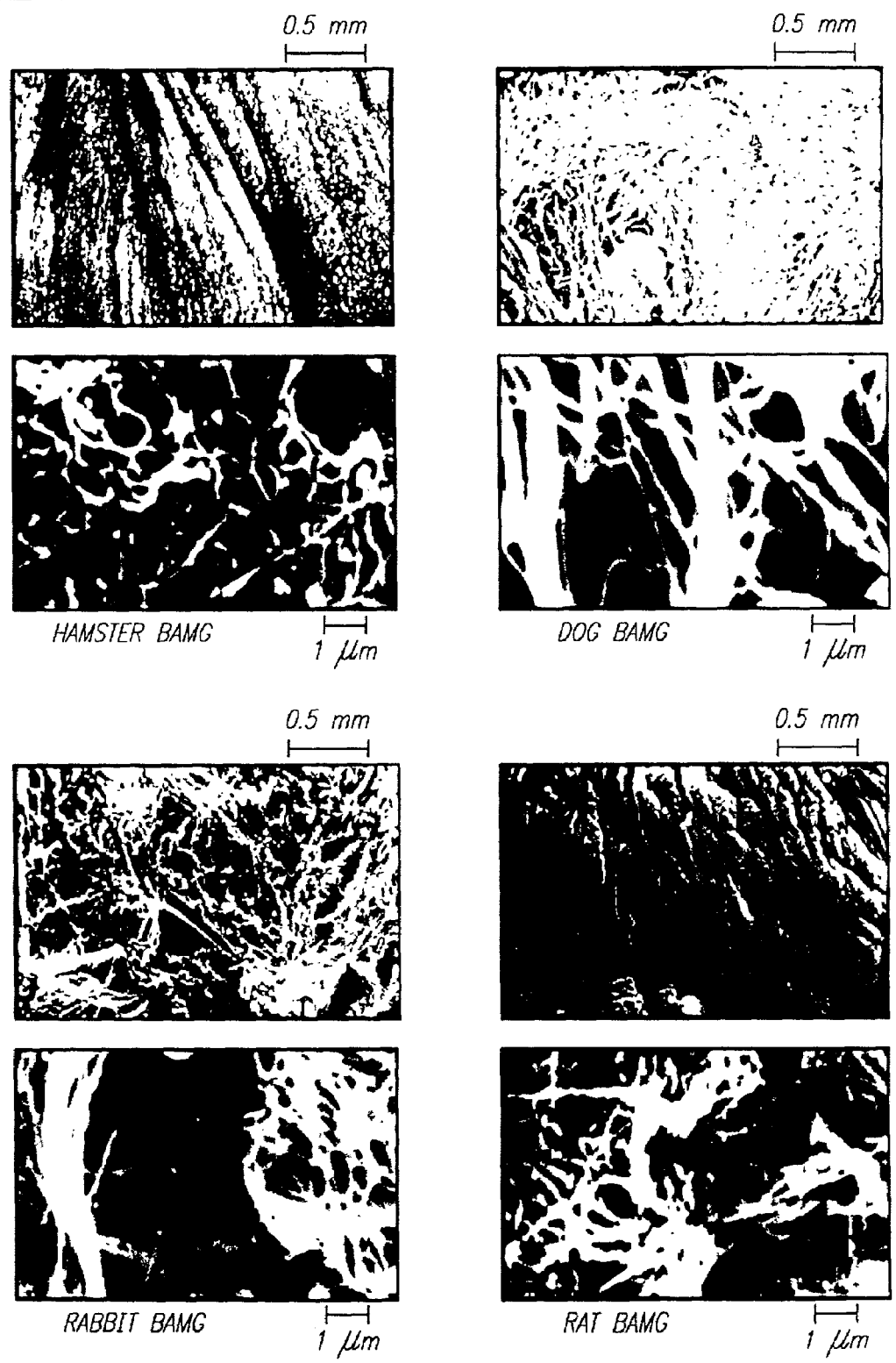
FIG. 3 shows the scanning electron microscopy of the dog, hamster, and rabbit BAMG at 20× and 5.000× magnification.

Supramaximal electrical field stimulation at increasing frequencies showed contractile responses in all BAMG-regenerated strips that were qualitatively very similar to the host bladder smooth muscle strips. Peak contractions uniformly occurred at a stimulation frequency of 40 pulses per second in both the regenerated and the host bladder strips (FIG. 3). The maximal force of contraction was almost the same in all BAMG-regenerated strips and amounted to 85% (dog BAMG), 42% (hamster BAMG) and 38% (rabbit BAMG) of the appropriate host bladder wall tissue (Table 4).

Carbachol stimulation ($1 \times 10^{-4}$M) also elicited a qualitatively identical contraction in the BAMG and host bladder strips. Again, the maximal force of contraction was the same in all BAMG-regenerated strips. This force amounted to 60% (dog BAMG), 50% (hamster BAMG) and 34% (rabbit BAMG) of the appropriate host bladder wall tissue and it was on average two-fold higher than the peak contractions evoked by electrical stimulation. Administration of atropine ($1 \times 10^{-6}$ M) completely relaxed all carbachol-contracted muscle strips even below their initial resting tension, also diminishing the response to subsequent electrical stimulation by more than 90% in all strips.

2.6 Solutions and Drugs

Krebs (mmol): NaCl 118.1, KCl 4.6, $MgSO_4$ 1.2, $KH_2PO_4$ 1.2, $NaHCO_3$ 25.0, $CaCl_2$ 2.5, glucose 11.0. In "high potassium" Krebs buffer solution (KCl 60 mM), NaCl was replaced with equimolar amounts of KCl. All solutions were made fresh from stock solutions. Carbachol (Sigma Chemical Co., St. Louis Mo.; C 4382) and atropine sulfate (Sigma A 0257) were diluted in saline. The amounts and volumes added to the bath were as follows: Carbachol $1 \times 10^{-4}$M, 1 mL; Atropine $1 \times 10^{-6}$M, 1 mL.

High-potassium (60 mmol) Krebs buffer solution caused sustained submaximal contraction in both the BAMG-regenerated and host bladder smooth muscle strips. The differences in maximal force of contraction in the grafted group were not statistically significant. Once more, peak contractions were smaller in the regenerated strips. They amounted to 86% (dog BAMG), 44% (rabbit BAMG) and 29% (hamster BAMG) of the appropriate host bladder wall tissue (Table 4).

2.7 Staining

After fixation with 10% formalin for at least 24 hours, the specimens for light microscopic examination were embedded in paraffin, sectioned and stained with trichrome for collagen and smooth muscle, hematoxylin and eosin (H&E) for nuclei, α-actin for smooth muscle and urothelium, and protein gene product (PGP) for nerves. Specimens were also prepared for scanning electron microscopy.

Macroscopically, the inflated bladders were uniformly dilated without evidence of diverticuli formation in the region of the graft. Mild to moderate adhesions to the surrounding tissue were found in all animals, including the partial cystectomy group, next to the identification sutures rather than within the matrix area itself. Within 4 months after surgery there seemed to be a reversal of the ratio of matrix area/host bladder area, suggesting significant autoregeneration of the host bladder and relative shrinkage of the BAMG. No macroscopic signs of hydronephrosis or other upper tract deterioration were noted at sacrifice in any of the animals.

Histologic staining of all dog, hamster and rabbit BAMG-regenerated bladders showed a bladder wall structure that was qualitatively identical to the host bladder because all three layers of normal rat bladder were present. The inner surface of the grafts was covered by a uniform urothelial lining with a differentiated muscularis mucosas, although most bladders had global urothelial hyperplasia resulting from stone formation. Distinct bundles of well developed, spatially oriented detrusor smooth musde were evident throughout the grafted area. The thickness of these muscle bundles seemed to decrease in the central part of the BAMGs, however. The number of well-formed blood vessels (small- and large-diameter) appeared greater in the BAMG-regenerated than in the host bladders. The opposite was true for PGP-positive nerve fibers. There were no mononuclear inflammatory cell infiltrates or other histologic signs of rejection in any of the BAMGs.

2.8 Statistics

A two-tailed Student's t-test was used to compare volumes per void, cystometric values and organ bath data in the control and grafted animals; p values<0.05 were considered statistically significant. All data are presented as mean±S.E.M.

What is claimed is:

1. An insoluble elastic matrix graft for repairing ureter or urethra smooth muscle having the following properties:
   (i) the matrix graft is derived from ureter or urethra smooth muscle tissue;
   (ii) the matrix graft is impermeable to urine;
   (iii) the matrix graft consists essentially of an intact framework of collagen and elastic fibers that is free of cell contents; and,
   (iv) the framework permits growth of muscle cells within the framework.

2. A matrix graft in accordance with claim 1, said matrix graft being prepare from tissue isolated from an animal selected from the group consisting of rat, rabbit, hampster, dog, pig and human.

3. A matrix graft in accordance with claim 1, said matrix graft being prepared from tissue isolated from an animal selected from the group consisting of rat, rabbit, hampster, dog, pig and human, and indicating essentially no cell nuclei when stained with a dye selected from the group consisting of trichrome, H&E, α-actin and PGP.

4. A matrix graft of claim 1 wherein the matrix graft is prepared using a combination of exogenous detergents and enzymes.

5. A matrix graft of claim 1 wherein the matrix is treated with a nuclease to remove nucleic acid.

* * * * *